(12) United States Patent
Yoshikawa et al.

(10) Patent No.: US 6,844,432 B2
(45) Date of Patent: Jan. 18, 2005

(54) POLYMORPHIC DNAS AND THEIR USE FOR DIAGNOSIS OF SUSCEPTIBILITY TO PANIC DISORDER

(75) Inventors: Takeo Yoshikawa, Saitama (JP); Eiji Hattori, Saitama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 10/013,329

(22) Filed: Dec. 7, 2001

(65) Prior Publication Data

US 2002/0160390 A1 Oct. 31, 2002

(51) Int. Cl.$^7$ .......................... C07H 21/02; C12Q 1/68
(52) U.S. Cl. .......................... 536/23.1; 536/24.3; 435/6
(58) Field of Search .............................. 536/23.1, 24.3; 435/6

(56) References Cited

U.S. PATENT DOCUMENTS 5,474,796 A * 12/1995 Brennan

OTHER PUBLICATIONS

Genbank AC018358[gi:6554213] , Dec. 12, 1999.*
Genbank AC018358[gi31126629], May 29, 2003.*
Bowen et al. "Linked Polymorphisms Upstream of Exons 1 and 2 of the Human Cholecystokinin Gene Are Not Associated with Schizophrenia or Bipolar Disorder" Molecular Psychiatry 3:67–71 (1998).
Bradwejn et al. "Cholecystokinin–Tetrapeptide Induces Panic Attacks in Patients with Panic Disorder" Can. J. Psychiatry 35:83–85 (1990).
Bradwejn et al. "Enhanced Sensitivity to Cholecystokinin Tetrapeptide in Panic Disorders—Clinical and Behavioral Findings" Arch. Gen. Psychiatry 48:603–610 (1991).
Bradwejn et al. "The Panicogenic Effects of Cholecystokinin–Tetrapeptide Are Antagonized by L–365,260, A Central Cholecystokinin Receptor Antagonist, in Patients With Panic Disorder" Arch. Gen. Psychiatry 51:486–493 (1994).
De Montigny et al. "Cholecystokinin Tetrapeptide Induces Panic–like Attacks in Healthy Volunteers" Arch Gen Psychiatry 46:511–517 (1989).

De Weerth et al. "Molecular Cloning, Functional Expression and Chromosomal Localization of the Human Cholecystokinin Type A Receptor" Biochemical and Biophysical Research Communications 194(2):811–818 (1993).
Hattori et al. "Identification of a Compound Short Tandem Repeat Stretch in the 5'–Upstream Region of the Cholecystokinin Gene, and Its Association with Panic Disorder but Not with Schizophrenia" Molecular Psychiatry 6:465–470 (2001).
Hökfelt et al. "Evidence for Coexistence of Dopamine and CCK in Meso–Limbic Neurones" Nature 285:476–478 (1980).
Moroji et al. "Antipsychotic Effects of Ceruletide (Caerulein) on Chronic Schizophrenia" Arch. Gen. Psychiatry 39:485–486 (1982).
Rasmussen et al. "Cholecystokinin (CCK) and Schizophrenia: The Selective $CCK_B$ Antagonist LY262691 Decreases Midbrain Dopamine Unit Activity" European Journal of Pharmacology 209:135–138 (1991).
Skre et al. "A Twin Study of DSM–III–R Anxiety Disorders" Acta Psychiatrica Scandinavica 88:85–92 (1993).
Wang et al. "Possible Association of A Cholecystokinin Promotor Polymorphism ($CCK_{36CT}$) With Panic Disorder" American Journal of Medical Genetics (Neuropsychiatric Genetics) 81:228–234 (1998).
Weissman et al. "The Cross–national Epidemiology of Panic Disorder" Arch. Gen. Psychiatry 54:305–309 (1997).

* cited by examiner

Primary Examiner—Jeffrey Fredman
(74) Attorney, Agent, or Firm—Morrison & Foerster LLP

(57) ABSTRACT

The present invention relates to a method for diagnosing panic disorder, said method being based on the determination of the class of polymorphism of the short tandem repeat (STR) complex in the upstream region of human cholecystokinin gene. The polymorphic DNA comprises a DNA sequence, having a general formula (1):

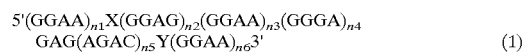

$$5'(GGAA)_{n1}X(GGAG)_{n2}(GGAA)_{n3}(GGGA)_{n4}GAG(AGAC)_{n5}Y(GGAA)_{n6}3' \quad (1)$$

wherein X denotes a DNA sequence of SEQ ID NO: 1, Y denotes a DNA sequence of SEQ ID NO:2 and each of n1, n2, n3, n4, n5 and n6 denotes independently 0 or a positive integral number, whereby said DNA ranging from 363 to 399 base pairs in length. The invention also relates to an assay kit used for implementing said method.

6 Claims, 2 Drawing Sheets

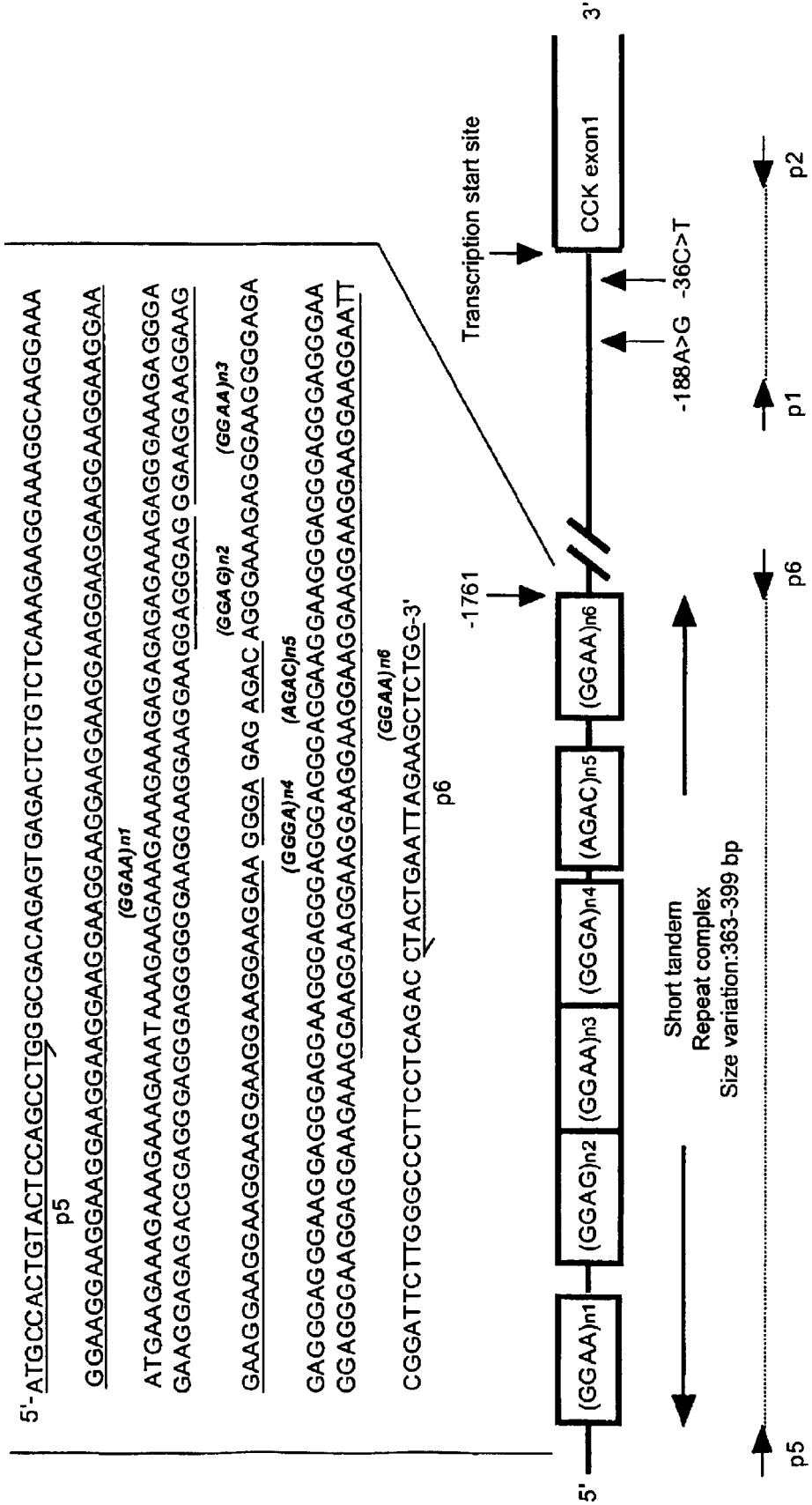
[Fig. 1]

[Fig. 2]
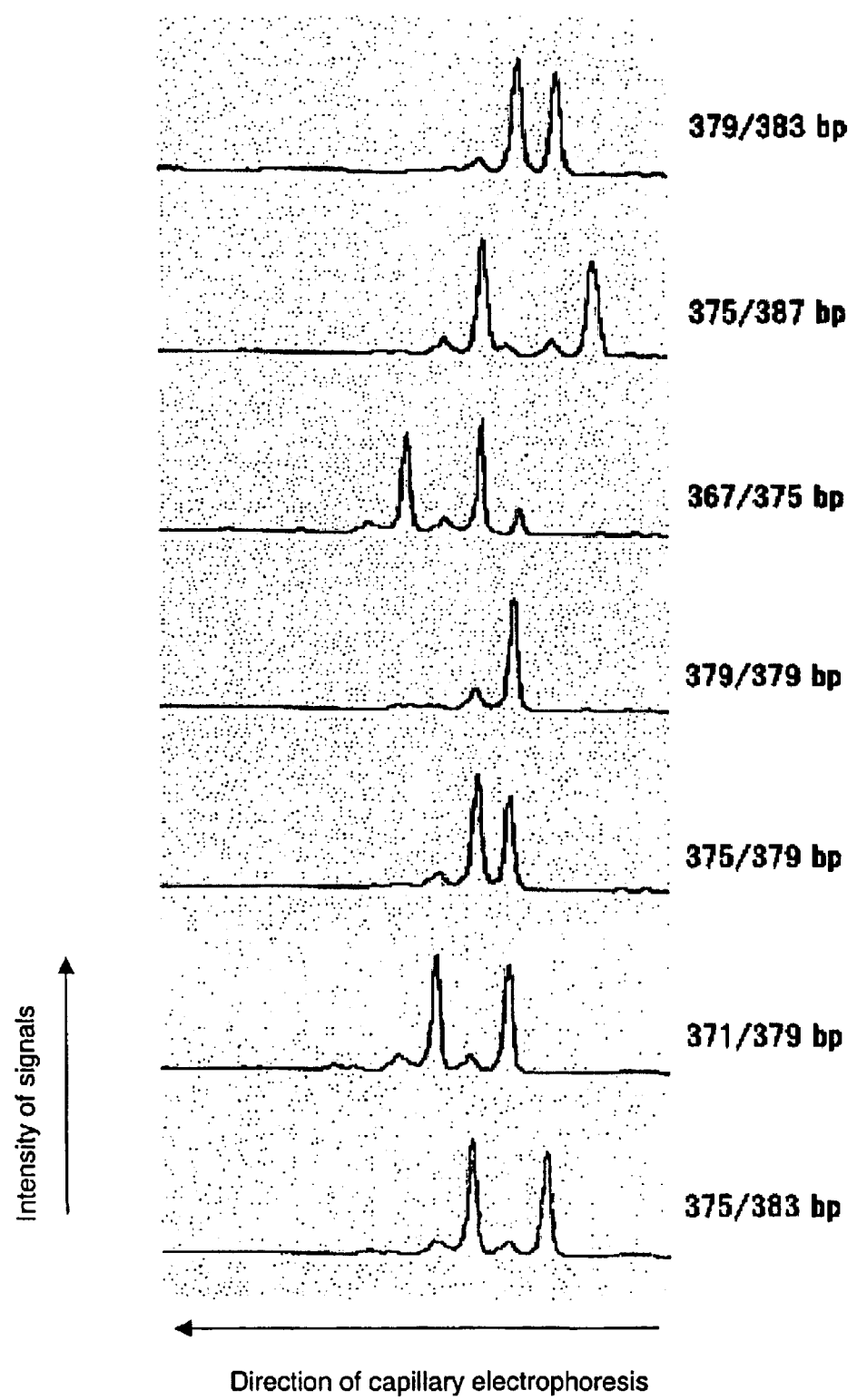

SEQUENCE LISTING

<160> NUMBER OF SEQ ID NOS: 9

<210> SEQ ID NO 1
<211> LENGTH: 108
<212> TYPE: DNA
<213> ORGANISM: Homo sapiens

```
<400> SEQUENCE: 1
atgaagaaag aaagaaagaa ataaagaaga aagaaagaaa gagagagaga aagagggaaa    60
gagggagaag gagagacgga gggagggagg ggggaaggaa ggaaggaa                 108

<210> SEQ ID NO 2
<211> LENGTH: 103
<212> TYPE: DNA
<213> ORGANISM: Homo sapiens

<400> SEQUENCE: 2
agggaaagag ggaagggagg agagggaggg aaggagggag gaagggaggg agggagggag    60
gaaggaaggg agggagggag ggaaggaggg aaggaggaag aaa                     103

<210> SEQ ID NO 3
<211> LENGTH: 300
<212> TYPE: DNA
<213> ORGANISM: Homo sapiens

<400> SEQUENCE: 3
ggggcgtggt ggctcacgcc tgtagtccca gcattttggg aggccaaggt gggtagatca    60
cctgaggtca gaagttcgag accaacctag ccaacatggt gaaccccttgt ctctactaaa  120 aatataaaaa ttagccaggc atggctgcac atgcctgtaa tcccagccgc tgggaggct    180 gaggcaggag aatcgtttga acctgggagg cagaggttgc agtgagccga gatcatgcca   240
ctgtactcca gcctgggcga cagagtgaga ctctgtctca aagaaggaaa ggcaaggaaa   300

<210> SEQ ID NO 4
<211> LENGTH: 300
<212> TYPE: DNA
<213> ORGANISM: Homo sapiens

<400> SEQUENCE: 4
ttcggattct tgggcccttc ctcagaccta ctgaattaga agctctgggg gtatttcgat    60
aacaagttta tgtttccaga catgtcttgc cacaatcaca aataagacta ttttcgcaac  120
tgaactacac aaaccttagc aggctcgtgg cgaaaccact ggaaagcatt taatcagctt   180
cagctctttc aaacatgttg cccataggtt gcagaaacgc agctgcctct caggattaga   240
aagtggagca gcaaccggag gcgtctctgg gccgcccccc caaccccccc accccgcctc   300

<210> SEQ ID NO 5
<211> LENGTH: 21
<212> TYPE: DNA
<213> ORGANISM: Artificial Sequence
<220> FEATURE:
<223> OTHER INFORMATION: Upstream primer p5

<400> SEQUENCE: 5
atgccactgt actccagcct g                                              21

<210> SEQ ID NO 6
<211> LENGTH: 21
<212> TYPE: DNA
<213> ORGANISM: Artificial Sequence
<220> FEATURE:
<223> OTHER INFORMATION: Downstream primer p6

<400> SEQUENCE: 6
ccagagcttc taattcagta g                                              21
```

```
<210> SEQ ID NO 7
<211> LENGTH: 20
<212> TYPE: DNA
<213> ORGANISM: Artificial Sequence
<220> FEATURE:
<223> OTHER INFORMATION: Upstream primer p1

<400> SEQUENCE: 7
aagcttctcg gacccagagg                                          20

<210> SEQ ID NO 8
<211> LENGTH: 20
<212> TYPE: DNA
<213> ORGANISM: Artificial Sequence
<220> FEATURE:
<223> OTHER INFORMATION: Downstream primer p2

<400> SEQUENCE: 8
gggcacaaag ctgaagacag                                          20

<210> SEQ ID NO 9
<211> LENGTH: 496
<212> TYPE: DNA
<213> ORGANISM: Homo sapiens

<400> SEQUENCE: 9
atgccactgt actccagcct gggcgacaga gtgagactct gtctcaaaga aggaaaggca    60
aggaaaggaa ggaaggaagg aaggaaggaa ggaaggaagg aaggaaggaa ggaaggaagg   120
aaggaaggaa atgaagaaag aaagaaagaa ataaagaaga aagaaagaaa gagagagaga   180
aagagggaaa gagggagaag gagagacgga gggagggagg ggggaaggaa ggaaggaagg   240
agggagggaa ggaaggaagg aaggaaggaa ggaaggaagg aaggaaggaa gggagagaga   300
cagggaaaga gggaaggga gagagggagg gaaggaggga ggaagggagg gagggaggga   360
ggaaggaagg gagggaggga gggaaggagg gaaggaggaa gaaaggaagg aaggaaggaa   420
ggaaggaagg aaggaaggaa ggaaggaatt cggattcttg ggcccttcct cagacctact   480
gaattagaag ctctgg                                                  496
```

POLYMORPHIC DNAS AND THEIR USE FOR DIAGNOSIS OF SUSCEPTIBILITY TO PANIC DISORDER

RELATED APPLICATIONS

This application claims priority to Japanese Patent Application No. 2000-375090, filed on Dec. 8, 2000.

FIELD OF THE INVENTION

The present invention relates to novel polymorphisms, and more specifically, to polymorphisms of the short tandem repeat type in the 5'-upstream region of human cholecystokinin gene, and their use, i.e. a method and a kit for diagnosis of susceptibility to panic disorder.

BACKGROUND OF THE INVENTION

Panic disorder is a common and genetically complex mental illness, characterized by recurrent and unexpected panic attacks. It exhibits a lifetime prevalence rate of between 1.2/100 to 2.4/100 in the general population (Weissman, M. M. et al., *Arch. Gen. Psychiatry,* 1997; 54, 305–309). Family studies have consistently shown a higher prevalence ranging from between 7.7% to 20.5% in the first-degree relatives of probands. Twin studies have shown concordance rates of 25% for MZ twins and 10% for DZ twins (Skre, I. et al., *Acta Psychiatr. Scand.* 1993; 88, 85–92). These epidemiological studies suggest involvement of genetic factors in the development of this disease.

Cholecystokinin (CCK) is a neuropeptide as well as a gastrointestinal peptide hormone, and is reported to have the relation with pathogenesis of panic disorder and schizophrenia. The carboxy terminal tetrapeptide of CCK (CCK-4), expressed in the brain, is thought to act as a neurotransmitter and/or neuromodulator. It provokes panic attacks in subjects with panic disorder and normal controls (Bradwejn et al., 1990; *Can. J. Psychiatry* 35, 83–85; and de Montigny et al., 1989; *Arch Gen Psychiatry* 46, 511–517). Patients with panic disorder have a higher sensitivity to CCK-4 than controls (Bradwejn et al., 1991; *Arch. Gen. Psychiatry* 48, 603–610). Furthermore, this panicogenic effect of CCK-4 is inhibited by antagonists of CCK B receptor (Bradwejn et al., 1994; *Arch. Gen. Psychiatry* 51, 486–493) which constitutes a large proportion of the CCK receptors in the human brain (de Weerth et al., 1993; *Biochem. Biophys. Res. Commun.* 194, 811–818). These findings have intensified research into elucidating the role of CCK in panic disorder.

CCK-like peptides, mainly the carboxy terminal octapeptide of CCK (CCK-8), co-localize with dopamine in mesolimbic dopaminergic neurons (Hokfelt et al., 1980; *Nature* 285, 476–478). In rats, CCK B receptor antagonists are shown to decrease the number of spontaneously active midbrain dopamine neurons (Rasmussen et al., 1991; *Eur. J. Pharmacol.* 209, 135–138). In humans, CCK-8 is reported to have an anti-psychotic effect (Moroji et al., 1982; *Arch. Gen. Psychiat.* 39, 485–486), inferring a possible role in the pathology of schizophrenia.

Two groups simultaneously reported a single nucleotide polymorphism (SNP), –36C>T in the 5'-upstream region of the CCK gene. Wang et al., (1998) *Am. J. Med. Genet. (Neuropsychiatr. Genet.)* 81, 228–234, showed that the –36T allele was weakly associated with subjects manifesting panic attacks (P<0.05) but not with panic disorder. In a case-control study of schizophrenia, Bowen et al., (1998) *Mol. Psychiatry* 3, 67–71, found no association between this SNP and the disease.

In general, the polymorphism, such as SNPs, which exists frequently in the human genome, is thought to have a relationship with a specific disease or constitution. Therefore, it is desirable to find the polymorphism which is used for the diagnosis and treatment of these diseases and to provide high quality order-made medical care. However, in the prior art, no functional polymorphisms associated with psychiatric disease have been reported in the CCK gene.

SUMMARY OF THE DISCLOSURE

It is, therefore, the present invention is directed to providing a method for diagnosing panic disorder and related useful methods therefor, by analyzing the structure of the human CCK gene, which is suggested to have a relationship with a psychiatric disease.

The present invention is further directed to providing a kit or a reagent for implementing said methods.

Recognizing the importance of the above objects, the present inventors have investigated the CCK gene. These efforts led to the discovery of a novel short tandem repeat (STR) complex, located in the 5'-upstream region of the CCK gene, and this STR was found to be polymorphic with ten different allele lengths. Analysis of the DNAs of many subjects showed that the distribution of the class of polymorphism is significantly different between patients with panic disorder and controls, and that the identification of the class of the polymorphism is useful for the diagnosis of panic disorder. These findings have led to the following inventions.

According to a first aspect of the present invention, there is provided an isolated DNA which is derived from an upstream region of a human cholecystokinin gene, said DNA comprising a polymorphic DNA sequence having a general formula (1):

$$5'(GGAA)_{n1}X(GGAG)_{n2}(GGAA)_{n3}(GGGA)_{n4}$$
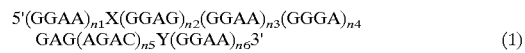
$$GAG(AGAC)_{n5}Y(GGAA)_{n6}3' \quad (1)$$

wherein X denotes a DNA sequence of SEQ ID NO:1, Y denotes a DNA sequence of SEQ ID NO:2 and each of n1, n2, n3, n4, n5 and n6 denotes independently 0 or a positive integral number, whereby said DNA ranging from 363 to 399 base pairs in length.

According to a second aspect of the present invention, there is provided a hybridization probe consisting essentially of said DNA as defined above.

According to a third aspect of the present invention, there is provided a method for determining a class of polymorphism of a short tandem repeat stretch in the 5'-upstream region of the human cholecystokinin gene, said method comprising:

a) obtaining a DNA sample from a subject;

b) amplifying the 5'-upstream region of the human cholecystokinin gene in the sample; and c) identifying the class of polymorphism by comparing the amplified DNA with the isolated DNA of the first aspect of the invention.

In preferred embodiments of this aspect of the invention, the class of polymorphism is detected by at least a method selected from the group consisting of sequence determination, gel electrophoresis, southern blotting, restriction fragment length polymorphism (RFLP) method, single strand conformational polymorphism (SSCP) method and mass spectrometry.

According to a fourth aspect of the invention, there is provided an assay kit for determining a class of polymorphism of a short tandem repeat stretch in the 5'-upstream region of the human cholecystokinin gene, said kit comprising:

a) a sense primer consisting of continuous 10 to 30 nucleotide sequence of SEQ ID NO:3; and b) an anti-sense primer consisting of continuous 10 to 30 nucleotide sequence complementary to the nucleotide sequence of SEQ ID NO:4.

According to a fifth aspect of the present invention, there is provided a method for diagnosing panic disorder, comprising:

a) obtaining from a subject a DNA sample comprising the short tandem repeat stretch in the 5'-upstream region of the human cholecystokinin gene; and b) identifying a class of polymorphism present in the subject, wherein a specific class is an indication that said subject may suffer from panic disorder.

According to a sixth aspect of the present invention, there is provided a method for demonstrating a predisposition to panic disorder, comprising:

a) obtaining from a subject a DNA sample comprising the short tandem repeat stretch in the 5'-upstream region of the human cholecystokinin gene; and b) identifying a class of polymorphism present in the subject, wherein a specific class is an indication of a predisposition to panic disorder in said subject.

According to a seventh aspect of the present invention, there is provided a method for predicting the efficacy of an anxiolytic drug for the treatment of panic disorders, comprising:

a) obtaining from a subject a DNA sample comprising the short tandem repeat stretch in the 5'-upstream region of the human cholecystokinin gene; and b) identifying the class of polymorphism present in the subject, wherein a specific class is an indication that said anxiolytic drug may be effective for the treatment of panic disorders.

BRIEF DESCRIPTION OF THE DRAWINGS

FIG. 1 shows the structure and sequence of the 5'-upstream region of the CCK gene from one sample of human genome (SEQ ID NO:9). The position of the novel short tandem repeat (STR) complex, its polymorphic constituents, and the position of two single nucleotide polymorphisms are shown. The structure of this figure is an example of the polymorphic sequence, and shows the case of n1=16, n2=2, n3=11, n4=1, n5=1 and n6=11. GenBank Accession No. AF274749 represents sequence from n1=16, n2=2, n3=11, n4=0, n5=1 and n6=11. P1, p2, p5, p6 are the primers used to amplify specified regions in example 1 and 2.

FIG. 2 shows the results of the capillary electrophoresis of the polymorphic DNA of the STR complex located in the 5'-upstream region of the human CCK gene, analyzed by ABI 3700 DNA Analyzer and GeneScan software.

PREFERRED EMBODIMENT OF THE INVENTION

The genetic polymorphism of the present invention is found to be in the short tandem repeat (STR) stretch, located in the 5'-upstream region of the human CCK gene. The DNA sequence of this STR complex has been partially known as a draft sequence of the human genome project (GenBank Accession No. AC018358), however, it has not yet known if the STR is polymorphic, and the detailed structure of the class of polymorphism is initially disclosed by the present application. The DNA sample including this STR complex can be cloned easily from the human chromosome DNA by various methods known in the art. For example, it can be cloned from the gene library constructed by various vectors such as λ phage, cosmid or plasmid, and preferably cloned by amplifying the 5'-upstream region of the human CCK gene with Polymerase Chain Reaction (PCR) as described in Examples of the present invention.

DNA amplification can be performed by any method known in the art, such as PCR technology. This technology relies on thermal strand separation followed by thermal dissociation. During this process, at least one primer per strand, cycling equipment, high reaction temperatures and specific thermostable enzymes are used (Saiki, et al., *Science*, 1985; 230, 1350–1354; Mullis and Faloona, *Methods in Enzymology*, 1987; 155, 335–351; U.S. Pat. Nos. 4,683,195 and 4,883,202). Alternatively, it is possible to amplify the DNA at a constant temperature (Nucleic Acids Sequence Based Amplification (NASBA) Kievits, T., et al., *J. Virol Methods*, 1991; 35, 273–286; and Malek, L. T., U.S. Pat. No. 5,130,238; and Strand Displacement Amplification (SDA), Walker, G. T. and Schram, J. L., European Patent Application Publication No. 0 500 224 A2; Walker, G. T., et al., *Nuc. Acids Res.*, 1992; 20, 1691–1696; and the like). Any sequencing method known to a person skilled in the art may be employed. In particular, it is advantageous to use an automated DNA sequencer. The sequencing is preferably carried out with a double-stranded template by means of the chain-termination method using fluorescent primers. An appropriate kit for this purpose is provided from PE Applied Biosystems (PE Applied Biosystems, Norwalk, Conn., USA).

The STR complex of the present invention which is located in the upstream region of the human CCK gene, can be represented by the following general formula (1):

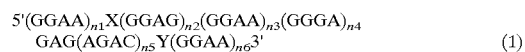

$$5'(GGAA)_{n1}X(GGAG)_{n2}(GGAA)_{n3}(GGGA)_{n4}GAG(AGAC)_{n5}Y(GGAA)_{n6}3' \quad (1)$$

wherein X denotes a DNA sequence of SEQ ID NO: 1, Y denotes a DNA sequence of SEQ ID NO:2 and each of n1, n2, n3, n4, n5 and n6 denotes independently 0 or a positive integral number, whereby said DNA ranging from 363 to 399 base pairs in length. The typical structure of the polymorphic DNA of the present invention which has these 6 repeating units, is shown in FIG. 1, and the number of repeats is variable by changing the numbers of n1 to n6. Therefore, the total length of the repeated sequence which constitutes the polymorphic DNA of the present invention, is in the range of 363 to 399 bp. Even if the repeated sequences are the same length, their constitution may be different. The polymorphic DNA of the present invention comprises at least the above DNA sequence. In addition, this DNA may contain several nucleotide sequences at both of its ends, such as the primer sequences, which are used for amplifying the polymorphic DNA of the present invention and the like. The flanking DNA sequence is shown in SEQ ID NO:3 with respect to the 5'-upstream region, and SEQ ID NO:4 with respect to the 3'-downstream region of the polymorphic DNA.

The use of the polymorphism of the STR complex of the present invention is not limited to a specific embodiment, but is applicable for various embodiments such as diagnosis and treatment of panic disorder by using, for example, as a probe, i.e., susceptibility or predisposition to panic disorder, and selection of an anxiolytic drug for the treatment of panic disorders based on the above diagnosis. In view of the physiological functions of CCK, it is also possible to develop a novel drug for other diseases by studying the mechanism of gene expression of human CCK gene with said polymorphic DNA. These drugs may be useful for diagnosis and treatment of Parkinson's disease, obesity, bulimia and gastrointestinal diseases such as gallbladder and biliary tract disorder.

The method for determining a class of polymorphism of the STR complex of the invention is carried out on a DNA sample from the subject. The DNA sample to be tested can be obtained from cells which have been withdrawn from the patient. These cells are preferably blood cells (for example mononucleated cells), which are easily obtained by the simple withdrawal of blood. Other cell types, such as fibroblasts, epithelial cells, keratinocytes, etc., can also be employed.

With regard to the method for determining a class of polymorphism of the STR complex, it can be used to compare the DNA sample from the subject, with the polymorphic DNA comprising the DNA sequence represented by said general formula (1) ranging from 363 to 399 base pairs in length. The useable techniques for comparing the extracted DNAs are direct sequencing, gel electrophoresis subsequent to southern hybridization, DNA amplification by using PCR method subsequent to gel electrophoresis, southern hybridization, the SSCP and RFLP techniques, and the like. A combination of more than two of the above methods are also appropriate. Gel separation techniques have the advantage of making it possible to discriminate between different alleles in terms of their size without it being necessary to sequence the DNA fragments. This technique is based on the migration, under denaturing conditions, of the denatured DNA fragments in a preferably polyacrylamide gel. As a similar technique, capillary electrophoresis and mass spectrometry can determine the DNA size. The bands can be visualized by any technique known to the skilled person, with the technique being based, for example, on the following: using labeled primers (fluorescence or radioactivity); introducing $\alpha$-$^{32}$PdCTP into the tested fragments; visualizing with ethidium bromide; or by means of hybridization (blotting) with a radiolabelled probe.

The single strand conformation polymorphism (SSCP) detection technique is also a method involving separation on an acrylamide gel, but under non-denaturing conditions. It is performed preferably with capillary electrophoresis equipment. This technique makes it possible to discriminate between different DNA fragments in terms of their conformation.

Alternatively, the DNA chip method can be employed (Baringa M., Science, 1991; 253, 1489; Bains, W., Bio/Technology, 1992; 10, 757–758; Wang et al., Science, 1998; 280, 1077–1082). These methods usually attach specific DNA sequences to very small specific areas of a solid support, such as micro-wells of a DNA chip. Each class of polymorphic DNA of the present invention can be used for the DNA chip when they are hybridized with the amplified DNA fragment of the subject, and then detected by the pattern of hybridization. Consequently, the comparison for determining the class of polymorphisms of the STR complex of the present invention means to identify a class of polymorphisms based on their nucleotide sequence, length of DNA fragments, and DNA three dimensional structure, or their sequence homology between the sample DNA and the probe DNA.

In one embodiment of the present invention, the STR complex region of the human CCK gene is amplified, and said amplified DNA is compared, as described above, to determine the class of polymorphism of the STR complex. With regard to the method of DNA amplification, the PCR method is commonly used, but it is also possible to amplify the DNA at a constant temperature. The primers which are used for the aforementioned DNA amplification can be synthesized by any technique known to a person skilled in the art, based on the unique sequence flanking to the STR complex region. The nucleotide sequence shown in SEQ ID NO:3 is the sequence of the 5'-upstream region of the STR complex. A single-stranded primer can be synthesized by selecting any continuous 10 to 30 base sequence from the sequence of SEQ ID NO:3. The nucleotide sequence shown in SEQ ID NO:4 is the sequence of the 3'-downstream region of the STR complex. Another single-stranded reverse primer can be synthesized by selecting any continuous 10 to 30 base sequence from the complement sequence of SEQ ID NO:4. The length of these oligonucleotide primers are commonly in the range of 10 to 30 nucleotides in length, preferably in the range of 18 to 25 nucleotides in length, and more preferably each primer is 21 nucleotides in length, shown as SEQ ID NO:5 and SEQ ID NO:6. Each of these lengths can be used in the present invention.

The reaction mixture for amplifying the DNA comprises 4 deoxynucleotide phosphates (dATP, dGTP, dCTP, dTTP) and heat stable DNA polymerase (such as Taq polymerase), which are all known to the skilled person in the art.

In a preferred embodiment of the present invention, the length of the amplified DNA is dependent on the class of the polymorphism sought to be identified. As is explained in detail hereafter, e.g., in example 3, the length of the upstream region of the STR complex is measured by gel electrophoresis. Any suitable Gel for electrophoresis, such as polyacrylamide, can be selected. In the case of polyacrylamide, the gel can be used in the range of 3% to 8% by concentration, preferably 4% to 5% by concentration of acrylamide. Capillary electrophoresis apparatus equipped with high performance polymer can also be used. It is a commonly used method for a person skilled in the art to determined the molecular weight of DNA fragments precisely by using suitable molecular weight markers.

The method of the present invention can be carried out by determining one of the alleles or genotype consisting of both alleles of the individual at the STR complex. The alleles are divided into three classes according to their length: Short (S) (363–375 base pairs), Medium (M) (379–383 base pairs) and Long (L) (387–399 base pairs). The polymorphic length of the alleles are related to a possible susceptibility to panic disorder. As shown in Table 2, described in detail in Example 4, the distribution of the M/M genotype are 17% in controls, but 34% in panic disorder which is twice that of the control. Thus, the individual of M/M genotype may have higher risk of panic disorder than those of other genotypes.

The accuracy of the diagnostic method of the present invention can be improved by combining it with any other method of diagnosis, including diagnoses of genetic element and serum protein. For example, other SNP markers are combined. As is described in detail in the Examples, the distribution of the haplotype, having both the M class of the STR complex and the two SNPs of the upstream of CCK gene (–188G and –36T), of panic disorder patients is significantly higher than that of the control. These results suggest that the combination of the diagnostic method of the present invention with that of other suitable polymorphisms improves the accuracy of the diagnosis of panic disorder.

According to a further aspect of the present invention, there is provided a method of order-made therapy, comprising the analysis of a predisposition for patients of panic disorder. Although the panic disorder is a complex illness associated with various causes, drugs such as antidepressants or benzodiazepines are mainly used for the treatment of the disease. However, there are many patients for whom these drugs have no therapeutic effect. The method of the present invention provides a novel and promising treatment to control the function of CCK in these patients.

An assay kit for determining a class of polymorphism of the STR complex of the present invention comprises oligonucleotide primers consisting of the unique sequence in the flanking regions of the STR complex. The nucleotide sequence shown in SEQ ID NO:3 is the sequence of the 5'-upstream region of the STR complex. A single-stranded primer can be synthesized by selecting any continuous 10 to 30 base sequence from the sequence of SEQ ID NO:3. The nucleotide sequence shown in SEQ ID NO:4 is the sequence of the 3'-downstream region of the STR complex. Another single-stranded reverse primer can be synthesized by selecting any continuous 10 to 30 base sequence from the complement sequence of SEQ ID NO:4. The length of these oligonucleotide primers are commonly in the range of 10 to 30 nucleotide length, preferably in the range of 18 to 25 nucleotides in length, and more preferably each 21 nucleotide length shown as SEQ ID NO:5 and SEQ ID NO:6 can be used. In addition to these primers, the assay kit comprises 4 deoxynucleotide phosphates (dATP, dGTP, dCTP, dTTP) and an effective amount of a nucleic acid producing catalyst. A number of biological enzymes are known in the art which are useful as polymerizing agents. These include, but are not limited to *E. coli* DNA polymerase I, Klenow fragment, bacteriophage T7 RNA polymerase, reverse transcriptase, and polymerases derived from thermophilic bacteria, such as *Thermus aquaticus*. The latter polymerases are known for their high temperature stability, and include, for example, the Taq DNA polymerase I. Other enzymes such as Ribonuclease H can be included in the assay kit for regenerating the template DNA.

EXAMPLES

The present invention is explained in more detail by reference to the following examples, however, they are not intended to restrict the scope of the present invention.

Example 1

Sequence Determination of the 5'-Upstream Region and the Discovery of a Polymorphic Short Tandem Repeat (STR) Complex Human genomic DNA was isolated from leukocytes using a DNA extraction kit (Stratagene, La Jolla, Calif., USA). Nielsen et al., (1996) *Cell Biol.* 15, 53–63, showed that the correct transcription start site of the CCK gene was located 9 bp upstream from the site originally reported by Takahashi et al., (1986) *Gene* 50, 353–360. We have employed a numbering system in which the former site was designated as +1. We have extended the 5'-flanking sequence approximately 2.3 kb beyond the previously reported 377 bp from the cap site, using the Genome Walker kit (Clontech, Palo Alto, Calif., USA) and consecutive PCR amplifications of genomic fragments. A polymorphic STR complex was located approximately −1.8 to −2.2 kb from the cap site (FIG. 1). PCR fragments were directly sequenced using the BigDye Terminator cycle sequencing kit (PE Applied Biosystems, Norwalk, Conn., USA) and an ABI 377 DNA sequencer (PE Applied Biosystems). Amplicons containing heterozygous STR stretches were subcloned into a TA vector (Invitrogen, Carlsbad, Calif., USA) and then sequenced.

The STR complex was located in the region 1.8 kb to 2.2 kb upstream from the transcription start site (capping site). The structure and sequence of the 5'-upstream region of the CCK gene from one sample of human genome was shown in FIG. 1. The newly determined 5'-upstream sequence of CCK gene has been deposited into GenBank under the accession No. AF274749.

Example 2

Polymorphism Screening of the Promoter Region of the Human CCK Gene

The 5'-flanking region, which potentially harbors promoter sequences, was amplified using the two primer pairs: upstream primer (p1) (SEQ ID NO:7)—5'AAGCTTCTCGGACCCAGAGG 3'(5'end at nt-233), and the downstream primer (p2) (SEQ ID NO:8)—5'GGGCACAAAGCTGAAGACAG 3'(5' end at nt+147). The PCR reactions were performed using the Expand Long PCR system (Buffer 1) (Roche, Mannheim, Germany) and the GeneAmp PCR system 9700 thermocycler (PE Applied Biosystems) with the cycling profile of an initial denaturation at 94° C. for 1 min, followed by 30 cycles of 94° C. for 15 sec, 63° C. for 30 sec, and 68° C. for 1 min, as well as a final extension at 68° C. for 5 min.

Example 3

Polymorphism Analysis of the 5'-Upstream Region of the Human CCK Gene

The diagnoses of panic disorder and schizophrenia were based on DSM III-R and DSM-IV, respectively (*AMERICAN PSYCHIATRIC ASS'N, DIAGNOSTIC AND STATISTICAL MANUAL OF MENTAL DISORDERS* 235–239 (3rd cd. rev. 1987), and 397–403 (4th cd. 1994) (American Psychiatric Press: Washington, DC)), and the patients were diagnosed by interview, requiring the consensus of at least two experienced psychiatrists. Panic patients consisted of 40 males, aged 22–80 years of age (mean age 43.2±12.5) and 33 females, aged 22–60 years (mean age 37.8 ±12.7). Schizophrenic patients consisted of 173 males, aged 18–80 years (mean age 45.6±12.5) and 132 females, aged 21–76 years (mean age 46.4±13.6). Control subjects were recruited from hospital staff documented to be free of psychoses, and company employees who showed no evidence of psychiatric problems during brief interviews by psychiatrists. The controls included 133 males (mean age 41.9±10.6) and 120 females (mean age 44.9±14.9). The present study was approved by the Ethics Committees of RIKEN and Tokyo Medical and Dental University, and all participants provided informed consent.

To amplify the region containing the STR complex in genomic DNA isolated from these subjects, a fluorescent dye-labeled upstream primer (p5), (SEQ ID NO:5) —5'ATGCCACTGTACTCCAGCCTG 3' (5' end at nt-2204), and a non-labeled downstream 10 primer (p6), (SEQ ID NO:6)—5'CCAGAGCTTCTAATTCAGTAG 3' (5' end at nt-1713), were used (FIG. 1). PCR was performed with an initial denaturation at 94° C. for 1 min, followed by 25 cycles at 97° C. for 10 sec, T° C. for 30 sec and 72° C. for 30 sec, and a final extension at 72° C. for 10 min, using Pyrobest DNA polymerase (Takara, Tokyo, Japan) and MasterAmp KN buffer (Epicentre Technologies, Madison, Wis., USA). The annealing temperature (T) was 62° C. in the first cycle and lowered 1° C. per cycle for the next nine cycles, and then fixed at 52° C. for the last 15 cycles.

PCR products were analyzed using an ABI 377 sequencer equipped with GeneScan software (PE Applied Biosystems).

Alleles which yielded different sized products were subcloned then sequenced.

As shown in FIG. 1, this STR complex was comprised of several types of repeat units, and the length polymorphisms were derived from the different number of tetranucleotide repeats, (GGAA)n, (GGAG)n, (GGGA)n, and (AGAC)n. According to the detailed analysis of the STR complex as shown in FIG. 1, there are six polymorphic repeat units in the STR, and in this study the following permutations of each repeat number were detected: n1=9, 12, 13, 16; n2=2, 3; n3=8, 9, 10, 11; n4=0, 1; n5=0, 1; n6=10, 11, 14, 15. Through genotyping, 10 different lengths of alleles in this STR (varying from 363 to 399 bp) were detected. (See FIG. 1 and Table 1). Extensive sequence analysis of alleles with the same length may reveal multiple variations within the tetranucleotide repeats of this STR.

The size of PCR products which have had their sequence's determined were analyzed by capillary electrophoresis using ABI 3700 DNA Analyzer and GeneScan software (PE Applied Biosystems) (FIG. 2). As shown in FIG. 2, each polymorphic DNA fragment can be identified as a distinct separated peak by capillary gel electrophoresis. In the figure, two peaks indicate that each allele has different polymorphic DNA, and one peak indicates that the length of each allele is the same.

TABLE 1

Size distribution of the short tandem repeat polymorphism

| Allele class<br>Allele size | Allele counts (Frequency) | | |
|---|---|---|---|
| | Panic disorder<br>(n = 73) | Schizophrenia<br>(n = 305) | Control<br>(n = 253) |
| S class | | | |
| 363 bp | 0 (0.00) | 3 (0.00) | 3 (0.01) |
| 367 bp | 3 (0.02) | 23 (0.04) | 19 (0.04) |
| 371 bp | 14 (0.10) | 50 (0.08) | 52 (0.10) |
| 375 bp | 43 (0.29) | 215 (0.35) | 162 (0.32) |
| M class | | | |
| 379 bp | 41 (0.28) | 149 (0.24) | 125 (0.25) |
| 383 bp | 38 (0.26) | 99 (0.16) | 86 (0.17) |
| L class | | | |
| 387 bp | 6 (0.04) | 45 (0.07) | 38 (0.08) |
| 391 bp | 0 (0.00) | 18 (0.03) | 16 (0.03) |
| 395 bp | 1 (0.01) | 5 (0.01) | 4 (0.01) |
| 399 bp | 0 (0.00) | 3 (0.00) | 1 (0.00) |
| P-value[a] | 0.025 | 0.94 | |

[a]Based on chi-square from table after collapsing together columns with small expected values. The assessment was performed using the Monte-Carlo simulation.

Example 4

Association Studies Using the STR Polymorphism

Differences of genotypic, allelic (in the cases for more than two alleles), and haplotypic distributions were assessed by the Monte-Carlo method using the CLUMP program (Sham P. C. et al., *Ann. Hum. Genet.* 1995; 59, 97–105) with 10000 simulations. P-values were calculated from the tables in which columns with small expected values were collapsed together. Odds ratios (OR) with a 95% confidence interval (CI) were estimated for the effects of high risk genotypes and alleles. Tests for Hardy-Weinberg equilibrium, the calculation of linkage disequilibrium (LD) between two loci, and the estimation of haplotype frequencies were carried out using Arlequin software (Schneider, S. et al., Arlequin ver.1.1: a software for population genetic data analysis. Genetics and Biometry Laboratory, University of Geneva, Switzerland).

The Monte-Carlo analysis showed a weak but significant difference in the STR allelic distributions between panic and control subjects (P=0.025) (Table 1). The alleles with 379 bp and 383 bp were more frequently represented in panic disorder than in controls. When the frequency of alleles with 379 bp and 383 bp was compared to that of the remaining alleles, there was a significant difference (P=0.003, $x^2$=8.7, d.f.=1) between the panic and control groups. Thus, we divided the alleles of the STR into three classes according to their length: short (S) (363–375 bp), medium (M) (379–383 bp) and long (L) (383–399 bp) classes (Table 1 and 2).

TABLE 2

Genotypic and allelic distributions of the short tandem repeat

| | Genotype or Allele counts (Frequency) | | |
|---|---|---|---|
| | Panic disorder<br>(n = 73) | Schizophrenia<br>(n = 305) | Control<br>(n = 253) |
| Genotype | | | |
| S/S | 13 (0.18) | 71 (0.23) | 57 (0.23) |
| M/M | 25 (0.34) | 50 (0.16) | 43 (0.17) |
| L/L | 0 (0.00) | 8 (0.03) | 4 (0.02) |
| S/M | 28 (0.38) | 121 (0.40) | 98 (0.39) |
| S/L | 6 (0.08) | 28 (0.09) | 24 (0.09) |
| M/L | 1 (0.01) | 27 (0.09) | 27 (0.11) |
| P-value | 0.0036 | 0.94 | |
| Allele | | | |
| S | 60 (0.41) | 291 (0.48) | 236 (0.47) |
| M | 79 (0.54) | 248 (0.41) | 211 (0.42) |
| L | 7 (0.05) | 71 (0.12) | 59 (0.12) |
| P-value | 0.0059 | 0.94 | |

This classification could be considered to have a rationale from a genetic point of view, since the grouped alleles are in linkage disequilibrium with neighboring SNPs (see the later section). The genotypic distributions based on these three categories were significantly different in the panic and control groups (P=0.0036) (Table 2). The OR for the M/M genotype versus the others was 2.54 (P=0.0014, $x^2$=10.2, d.f.=1, 95% CI=1.43–4.53). Allelic distributions were also significantly different between the two groups (P=0.0059). And, the OR for the M allele versus the others was 1.73, (P=0.0079, $x^2$=7.07, d.f.=1, 95% CI=1.19–2.50).

Example 5

Linkage Disequilibrium (LD) Analysis of the Markers, and Haplotype Analysis

Neither genotypic nor allelic distributions of the −188A>G and −36C>T polymorphisms were different in panic and control subjects and between schizophrenia and control groups (data not shown). However, the analysis of these two SNPs (−188A>G and −36C>T loci) showed a strong Linkage disequilibrium in panic (D'=1.0), schizophrenia (D'=0.99) and control sample (D'=0.91) as shown in Table 3. Significant LD existed between the three STR allele categories and each of the −188A>G and −36C>T SNPs (Table 4). This result provides a genetic basis for the classification of the ten STR alleles into three groups. In table 3 and 4, D values indicate deviation from linkage equilibrium (D=h-p1p2; h,haplotype frequency; p1,p2, frequencies for two alleles at two loci). D'(=D/Dmax) is the normalized linkage disequilibrium statistic, which lies in the range of −1 to 1 with the greater value indicating stronger linkage disequilibrium. P-values are calculated from estimated haplotype frequencies.

A comparison of the haplotypes defined by the STRs and the SNPs, −188A>G and −36C>T, showed that the distributions differed significantly between panic and control groups (p=0.0003) (refer to Table 5). The haplotype consisting of the STR M class, −188G and −36T was significantly more frequent in panic than control groups (p=0.01, $x^2$=10.8, d.f.=1). The haplotypic distributions between schizophrenics and controls showed a significant difference (p=0.02)(Table 5), but no single haplotype appeared to be significantly more frequent in schizophrenics than in controls.

TABLE 3

Linkage disequilibrium between two SNPs

|  | −188A > G vs −36C > T | | |
|---|---|---|---|
|  | D | D' | P-value |
| Panic disorder (n = 71) | 0.14 | 1.00 | <0.0001 |
| Schizophrenia (n = 305) | 0.15 | 0.99 | <0.0001 |
| Control (n = 253) | 0.14 | 0.91 | <0.0001 |

TABLE 4

Linkage disequilibrium between STR and SNPs

|  | STR vs SNPs | | | | | | |
|---|---|---|---|---|---|---|---|
|  |  | −188A > G | | | −36C > T | | |
|  | STR | D | D' | P-value | D | D' | P-value |
| Panic disorder (n = 71) | S | 0.05 | 0.30 |  | 0.04 | 0.42 |  |
|  | M | −0.06 | −0.32 | <0.021 | −0.04 | −0.40 | <0.041 |
|  | L | 0.01 | 0.50 |  | 0.00 | 0.17 |  |
| Schizophrenia (n = 305) | S | 0.00 | −0.02 |  | 0.01 | 0.08 |  |
|  | M | 0.03 | 0.14 | <0.0011 | 0.03 | 0.23 | <0.0001 |
|  | L | −0.02 | −0.34 |  | −0.04 | −0.44 |  |
| Control (n = 253) | S | −0.03 | −0.12 |  | −0.01 | −0.05 |  |
|  | M | 0.05 | 0.25 | <0.0001 | 0.03 | 0.27 | <0.0001 |
|  | L | −0.02 | −0.34 |  | −0.03 | −0.31 |  |

TABLE 5

Haplotype distributions

| Haplotype (STR/−188/−36) | Estimated haplotype frequency | | |
|---|---|---|---|
|  | Panic disorder (n = 71) | Schizophrenia (n = 305) | Control (n = 253) |
| S-A-C | 0.294 | 0.257 | 0.217 |
| S-A-T | 0.000 | 0.000 | 0.000 |
| S-G-C | 0.061 | 0.098 | 0.108 |
| S-G-T | 0.060 | 0.122 | 0.141 |
| M-A-C | 0.267 | 0.247 | 0.262 |
| M-A-T | 0.000 | 0.000 | 0.007 |
| M-G-C | 0.101 | 0.072 | 0.067 |
| M-G-T | 0.174 | 0.087 | 0.082 |
| L-A-C | 0.030 | 0.040 | 0.033 |
| L-A-T | 0.000 | 0.002 | 0.009 |
| L-G-C | 0.000 | 0.007 | 0.024 |
| L-G-T | 0.012 | 0.067 | 0.050 |
| P-value | 0.0003 | 0.020 |  |

In the present invention, the finding of a novel STR complex in the CCK gene and the strong association between polymorphisms of this STR and panic disorder provides the possibility of diagnosing panic disorder based on a biological (genetic) etiology. The invention also makes it possible to speculate the effective drug for the treatment of panic disorder. Furthermore, as the pathogenesis of panic disorder relates to many factors, the identification of the predisposition of panic disorder makes it possible to prevent the onset of the disease by removing the related factors. Still further, the present invention warrants functional studies to examine whether a differential enhancer-like effect can be induced by the polymorphic length of the STR. These studies will provide a screening system of binding factors (agonist or antagonist) for the regulatory site of CCK gene expression, and may lead to the development of a novel drug.

The present disclosure relates to the subject matter contained in Japanese Patent Application No. 2000-375090, filed on Dec. 8, 2000, and original research article *Molecular Psychiatry* 2001, 6, 465–470 published on July, 2001 which are expressly incorporated herein by reference in their entirety.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

All references cited herein are hereby incorporated by reference in their entireties, whether previously specifically incorporated or not.

What is claimed is:

1. An isolated DNA which is derived from the upstream region of the human cholecystokinin gene, said DNA consisting of a polymorphic DNA sequence, having a general formula (1):

$$5'(GGAA)_{n1}X(GGAG)_{n2}(GGAA)_{n3}(GGGA)_{n4}GAG(AGAC)_{n5}Y(GGAA)_{n6}3' \quad (1)$$

wherein X denotes a DNA sequence of SEQ ID NO:1, Y denotes a DNA sequence of SEQ ID NO:2 and each of n1, n2, n3, n4, n5 and n6 denotes independently 0 or a positive integral number, whereby said DNA ranges from 363 to 399 base pairs in length.

2. A hybridization probe consisting of said DNA as defined in claim 1.

3. A method for determining a class of polymorphism of a short tandem repeat stretch in the 5'-upstream region of the human cholecystokinin gene, said method comprising:
   a) obtaining a DNA sample from a subject;
   b) amplifying the 5'-upstream region of the human cholecystokinin gene in the sample; and
   c) identifying the class of polymorphism by comparing the amplified DNA with said DNA of claim 1.

4. The method of claim 3, wherein said class of polymorphism is detected by at least one method selected from the group consisting of sequence determination, gel electrophoresis, southern blotting, a restriction fragment length polymorphism (RFLP) method, a single strand conformational polymorphism (SSCP) method, and mass spectrometry.

5. The method of claim 3, wherein the 5'-upstream region of the human cholecystokinin gene in the sample is amplified by PCR with a sense primer consisting of SEQ ID NO:5 and an anti-sense primer consisting of SEQ ID NO:6.

6. An assay kit for determining a class of polymorphism of a short tandem repeat stretch in the 5'-upstream region of the human cholecystokinin gene, said kit comprising a sense primer consisting of SEQ ID NO:5 and an anti-sense primer consisting of SEQ ID NO:6.

* * * * *